US00PP36998P2

(12) United States Plant Patent
van Geest

(10) Patent No.: US PP36,998 P2
(45) Date of Patent: Oct. 7, 2025

(54) ***FICUS* PLANT NAMED 'ESFIBU1801'**

(50) Latin Name: ***Ficus benjamina* L.**
Varietal Denomination: ESFIBU1801

(71) Applicant: J. Van Geest Holding B.V., 's Gravenzande (NL)

(72) Inventor: Jan van Geest, 's Gravenzande (NL)

(73) Assignee: J. VAN GEEST HOLDING B.V., 's Gravenzande (NL)

( * ) Notice: Subject to any disclaimer, the term of this patent is extended or adjusted under 35 U.S.C. 154(b) by 0 days.

(21) Appl. No.: 18/831,405

(22) Filed: Jan. 15, 2025

(51) Int. Cl.
*A01H 5/12* (2018.01)
*A01H 6/00* (2018.01)

(52) U.S. Cl.
USPC ..... Plt./211
CPC ..... *A01H 6/00* (2018.05); *A01H 5/12* (2013.01)

(58) Field of Classification Search
USPC ..... Plt./211
CPC ..... A01H 6/00; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct variety of *Ficus* plant named 'ESFIBU1801' which is characterized by the combination of a compact and freely-branching growth habit, an abundance of relatively small narrow ovate to lanceolate foliage with a relatively long apiculate to aristate leaf apex, dark green foliage that is broadly margined with a light yellow-green in juvenile foliage and a lighter shade of green in mature foliage, and the stability of these characteristics from generation to generation.

2 Drawing Sheets

Latin name of the genus and species: The Latin name of the genus and species of the novel variety disclosed herein is *Ficus benjamina* L.

Variety denomination: The inventive variety of *Ficus* disclosed herein has been given the variety denomination 'ESFIBU1801'.

BACKGROUND OF THE INVENTION

Parentage: 'ESFIBU1801' is a spontaneous whole-plant mutation which was discovered growing amongst a cultivated population of *Ficus benjamina* 'Anastasia' (not patented). The inventor first observed the mutation in the summer of 2020 at their commercial greenhouse located in 's-Gravenzande, The Netherlands. The mutation was noted for its compact and freely-branched growth habit with small lanceolate leaves that have a unique, highly contrasted dark green and light yellow-green to light green variegated coloration. The plant was isolated for further evaluation to confirm the distinctness and stability of the characteristics first observed. Upon confirmation of distinctness and stability, the new *Ficus* plant was selected for commercialization and given the name 'ESFIBU1801'.

Asexual Reproduction: Asexual reproduction of the new cultivar 'ESFIBU1801', by way of vegetative division was first initiated in the late summer of 2020 at a commercial greenhouse in 's-Gravenzande, The Netherlands. Through five subsequent generations of asexual reproduction, the unique features of this cultivar have proven to be stable and true to type.

SUMMARY OF THE INVENTION

The cultivar 'ESFIBU1801' has not been observed under all possible environmental conditions. In and of itself, the phenotype may be altered somewhat with changes in environment such as temperature, water availability, and light intensity, without any variance in the genotype. The following traits have been repeatedly observed and are determined to be the unique characteristics of 'ESFIBU1801'. These characteristics in combination distinguish 'ESFIBU1801' as a new and distinct *Ficus* cultivar:

1. *Ficus* 'ESFIBU1801' exhibits an abundance of relatively small leaves, with a somewhat relaxed attitude, borne on a relatively compact and freely-branching plant; and
2. *Ficus* 'ESFIBU1801' exhibits narrow ovate to lanceolate foliage with a relatively long narrow apiculate to aristate leaf apex; and
3. *Ficus* 'ESFIBU1801' exhibits variegated foliage that is centered with a dark green and broadly margined with yellow-green in juvenile foliage and a lighter shade of green in mature foliage.

BOTANICAL DESCRIPTION OF THE PLANT

Figure 1:
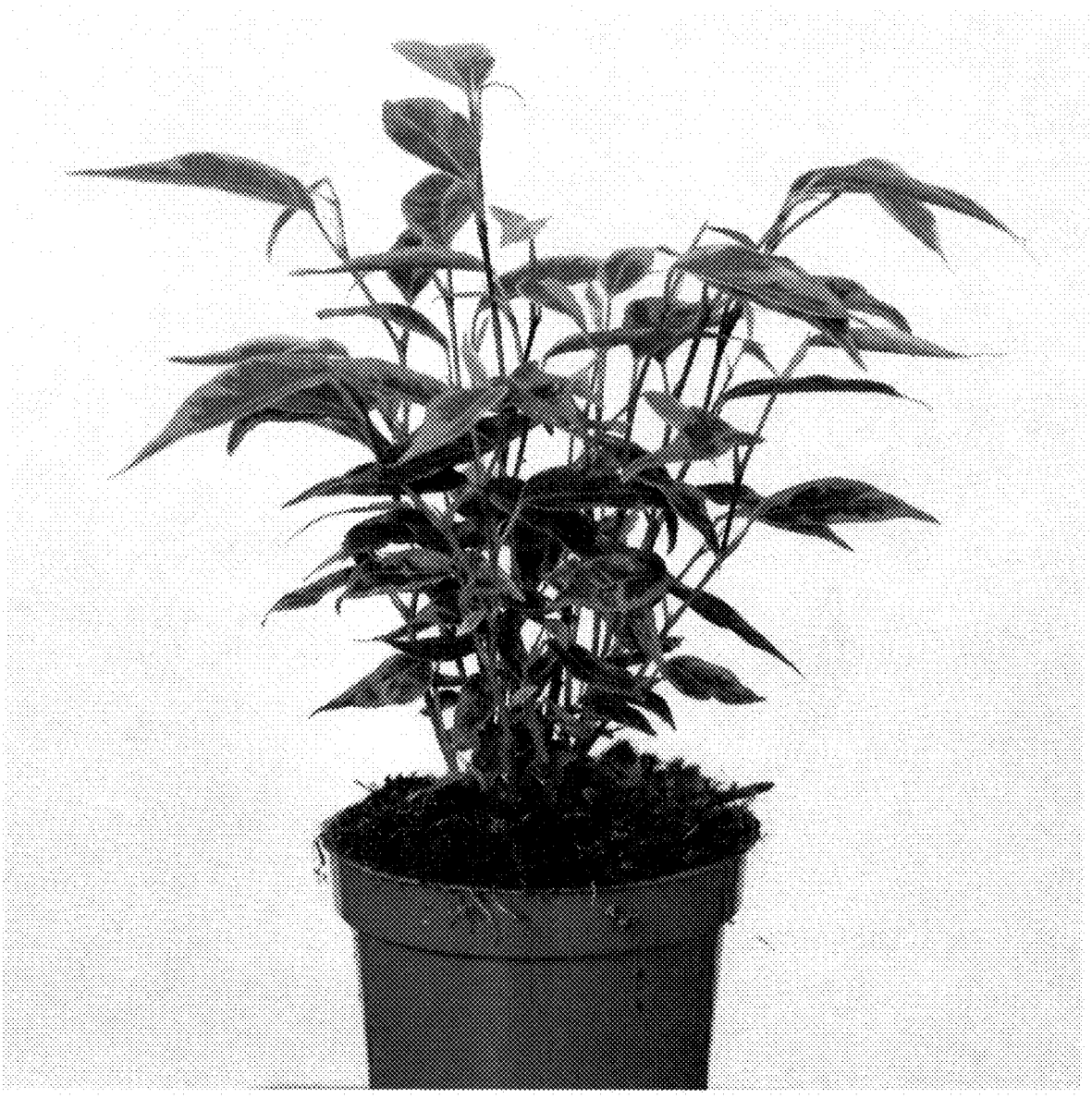
FIG. 1 illustrates, as nearly true as it is reasonably possible to make the same in color photographs of this type, an exemplary plant of 'ESFIBU1801' grown in a commercial greenhouse in 's-Gravenzande, The Netherlands. This plant is approximately 12 months old, planted in an 8 cm container.
Figure 2:
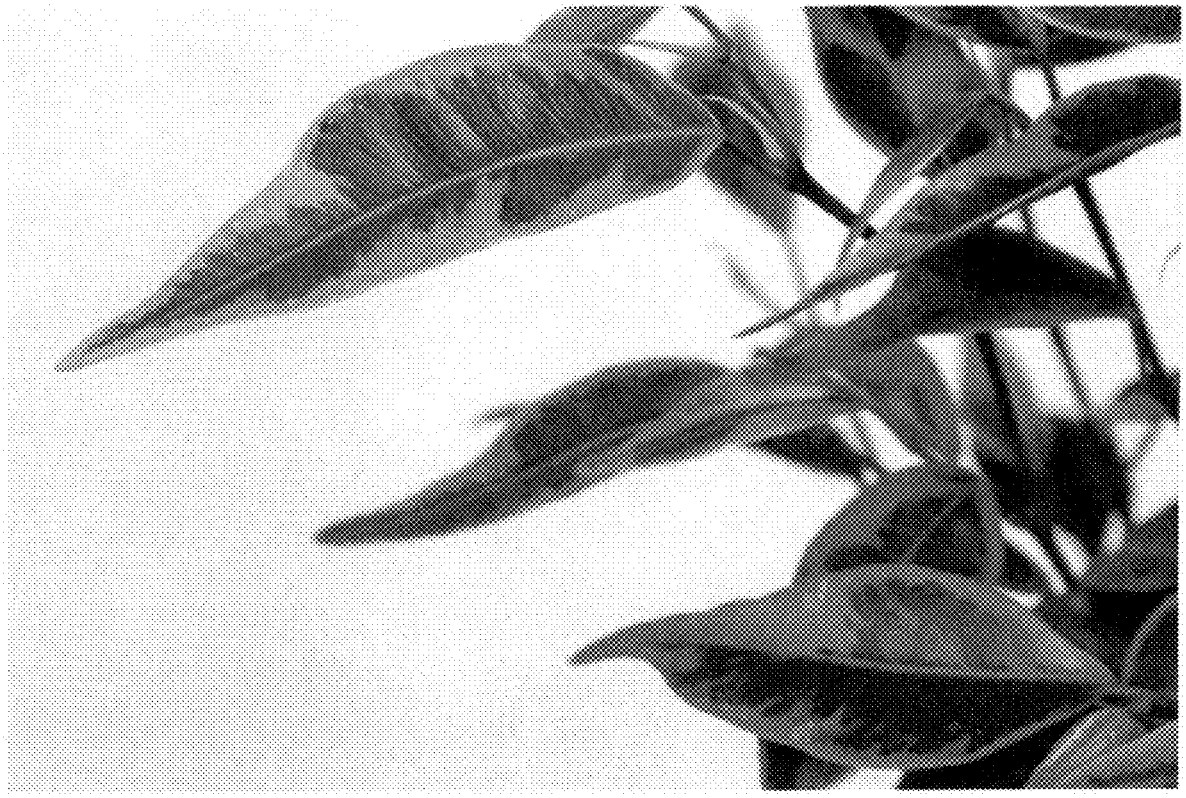
FIG. 2 illustrates, as nearly true as it is reasonably possible to make the same in color photographs of this type, the typical foliage of 'ESFIBU1801'.

The following observations and measurements were made in April of 2024 and describe a sample set of six 12-month-old 'ESFIBU1801' plants grown in 8 cm nursery pots at a greenhouse in 's-Gravenzande, The Netherlands. The plants were produced successfully without supplemental fertilizer or pest control measures in a greenhouse with full sun exposure. Water availability was provided by tidal irrigation, and no supplemental lighting was used.

Those skilled in the art will appreciate that certain characteristics will vary with older or, conversely, with younger plants. 'ESFIBU1801' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, Second Edition.

A botanical description of 'ESFIBU1801' as well as comparisons with the parent plant and most similar commercial variety of *Ficus* are provided below.

Plant description:

*Growth habit*.—Broad, upright to spreading perennial evergreen.

*Plant form*.—Obovate.

*Average height*.—15.5 cm.

*Plant spread*.—19.4 cm.

*Propagation*.—Type — Asexual propagation is accomplished by way of stem cuttings. Time to produce a rooted cutting — Approximately 40 days to produce a rooted cutting at approximately 25 degrees Celsius. Time to produce a finished plant — Approximately 15 weeks to produce a marketable finished plant in a 14 cm pot.

*Disease resistance*.—'ESFIBU1801' is not known to be susceptible or resistant to any diseases or insect pests.

*Environmental tolerances*.—Adapt to temperatures as high as 40 degrees Celsius; moderate to high tolerance to rain; moderate tolerance to wind.

Root system:

*General*.—Moderately dense, moderately branched rooting; roots are slightly fibrous.

*Distribution in the soil profile*.—Moderately deep.

*Diameter of roots*.—1.0 mm, on average.

*Texture*.—Smooth and glabrous.

*Color*.—Greyed-yellow, nearest to a combination of RHS 160C and 160D.

Stem:

*General branching habit*.—Basally branching main stems; with lateral branching. Stems produce milky exudate when damaged.

*Color of developing stems*.—Yellow-green, nearest to RHS 146B.

*Color of mature stems*.—Yellow-green, nearest to a mixture of RHS 148A and 148B.

*Color at internodes*.—Yellow-green, nearest to a mixture of RHS 148A and 148B.

*Color, oldest wood*.—Greyed-green, nearest to RHS 197A, and striated with grey-brown, nearest to a combination of RHS 199C and 199D.

*Texture*.—Glabrous, moderately covered with small lenticels.

*Luster*.—Slightly glossy.

*Main stem*.—Quantity — 13. Length — 12.2 cm. Diameter — 2.0 cm. Internode length — 1.9 cm. Attitude — Upright. Aspect — 80-degree angle from horizontal. Strength — Strong.

*Lateral branches*.—Quantity — 12. Length — 12.2 cm. Diameter — 2.0 cm. Internode length — 1.9 cm. Attitude — 30-degree angle from the main stems. Strength — Moderately strong.

*Lenticels*.—Shape — Elliptic. Length — 0.5 mm. Diameter — 0.3 mm. Color — Grey-brown, nearest to a color combination of RHS 199C and 199D.

Foliage:

*Quantity*.—7 leaves per lateral branch.

*Arrangement*.—Alternate.

*Attachment*.—Petiolate.

*Division*.—Simple.

*Lamina*.—Shape — Narrow ovate to lanceolate. Length — 5.0 cm. Width — 1.7 cm. Apex — Narrow apiculate to aristate; leaf tip is long relative to the total length of the lamina. Base — Acute. Aspect — Slightly carinate. Attitude — Relaxed; at an average angle of 40 degrees to the branch. Margin — Entire, slightly repand. Texture and luster of the adaxial surface — Glabrous and slightly glossy. Texture and luster of the abaxial surface — Glabrous and matte. Color — Juvenile foliage, adaxial surface — Green, nearest to RHS 143A, and broadly and irregularly margined with yellow-green nearest to RHS N144A. Juvenile foliage, abaxial surface — Nearest to a mixture of green and yellow-green, RHS 143A and 146A, and broadly and irregularly margined with a lighter shade of yellow-green, nearest to RHS 145A. Mature foliage, adaxial surface — Green, nearest to a mixture of RHS NN137A and 139A, and broadly and irregularly margined with a lighter shade of green, nearest to in between RHS 143A and 143B. Mature foliage, abaxial surface — Yellow-green, nearest to RHS 147B, and broadly and irregularly margined with a lighter shade of yellow-green, nearest to in between RHS 144A and 144B. Venation — Pattern — Pinnate. Color — Juvenile foliage, adaxial surface — Yellow-green, nearest RHS 144A. Juvenile foliage, abaxial surface — Yellow-green, nearest to RHS N148A. Mature foliage, adaxial surface — Yellow-green, nearest RHS 144A. Mature foliage, abaxial surface — Yellow-green, nearest RHS 144A.

*Stipule*.—Arrangement — At the base of each lateral branch; stipules are self-cleaning and drop shortly after the maturation of the lateral branches. Quantity — 2 per branch. Shape — Filiform. Length — 1.0 cm. Width — 0.7 mm. Color — Yellow-green, nearest to RHS 150D; at the apex of each stipule is greyed-purple coloring, nearest to RHS 186C.

*Petiole*.—Length — 1.0 cm. Diameter — 0.1 cm. Strength — Strong. Texture — Smooth; glabrous. Luster — Very slightly glossy. Color, adaxial surface — Yellow-green, nearest to RHS 146B. Color, abaxial surface — Yellow-green, nearest to RHS 146C.

Inflorescence: No flowering has been observed to date.

COMPARISON WITH THE PARENT PLANT

Plants of the new cultivar 'ESFIBU1801' differ from the parent, *Ficus benjamina* 'Anastasia' (not patented), in the following characteristics described in Table 1 below.

TABLE 1

| Characteristic | 'ESFIBU1801' | 'Anastasia' |
|---|---|---|
| Branching habit. | More freely-branching than 'Anastasia'. | Less lateral branching compared to 'ESFIBU1801' |
| Foliage abundance. | More abundant than 'Anastasia'. | Less abundant than 'ESFIBU1801'. |
| Foliage shape. | Narrow ovate to lanceolate, with a relatively long narrow apiculate to aristate apex. | Lanceolate to elliptic, with a relatively short apiculate apex. |
| General coloration of the foliage. | Variegated, with a darker shade of green in the central zone of the lamina relative to 'Anastasia', which yields a higher contrast with the coloration of the marginal zone. | Variegated, with a lighter shade of green in the central zone of the lamina relative to 'ESFIBU1801', which yields less contrast with the coloration of the marginal zone. |

TABLE 2

| Characteristic | 'ESFIBU1801' | 'ESFIBE1801' |
|---|---|---|
| Plant height. | Shorter than 'ESFIBE1801'. | Taller than 'ESFIBU1801'. |
| Branching habit. | More freely-branching than 'ESFIBE1801'. | Less lateral branching compared to 'ESFIBU1801' |
| Foliage size. | Smaller than 'ESFIBE1801'. | Larger than 'ESFIBU1801'. |
| Foliage shape. | Narrow ovate to lanceolate, with a relatively long narrow apiculate to aristate apex. | Narrowly ovate to oblong, with a relatively short aristate to caudate apex. |
| General coloration of the adaxial surface of the mature foliage. | Variegated; dark green and broadly margined with a lighter shade of green. | Not variegated; homogenously dark green. |

COMPARISON WITH THE CLOSEST KNOWN COMPARATOR

Plants of the new cultivar 'ESFIBU1801' are similar to the cultivar, *Ficus* 'ESFIBE1801', (U.S. Plant Pat. No. 31,962). A comparison of 'ESFIBU1801' with *Ficus* 'ESFIBE1801' is described in Table 2 below.

That which is claimed is:

1. A new and distinct variety of *Ficus* plant named 'ESFIBU1801', substantially as described and illustrated herein.

* * * * *